US012788375B2

(12) United States Patent
Kopp et al.

(10) Patent No.: US 12,788,375 B2
(45) Date of Patent: Nov. 10, 2026

(54) NEEDLE ATTACHMENT FOR A SPINAL NEEDLE

(71) Applicant: B. Braun Melsungen AG, Melsungen (DE)

(72) Inventors: Florin Kopp, Schortens (DE); Franziska Rieken, Kassel (DE); Dominik Schlemme, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 234 days.

(21) Appl. No.: 18/565,710

(22) PCT Filed: Jun. 1, 2022

(86) PCT No.: PCT/EP2022/064893
§ 371 (c)(1),
(2) Date: Nov. 30, 2023

(87) PCT Pub. No.: WO2022/253892
PCT Pub. Date: Dec. 8, 2022

(65) Prior Publication Data

US 2024/0268798 A1 Aug. 15, 2024

(30) Foreign Application Priority Data

Jun. 2, 2021 (DE) ..................... 10 2021 205 601.6

(51) Int. Cl.
*A61B 10/00* (2006.01)
*A61B 17/00* (2006.01)

(52) U.S. Cl.
CPC .. *A61B 10/0045* (2013.01); *A61B 2010/0077* (2013.01); *A61B 2017/00907* (2013.01)

(58) Field of Classification Search
CPC ....... A61M 25/0097; A61B 2010/0077; A61B 10/0045
See application file for complete search history.

(56) References Cited

U.S. PATENT DOCUMENTS 5,496,281 A * 3/1996 Krebs ................ A61M 25/065 604/168.01
6,656,161 B2 12/2003 Young et al.
(Continued)

FOREIGN PATENT DOCUMENTS

CN 204971325 U 1/2016
DE 102008017807 A1 10/2009
(Continued)

OTHER PUBLICATIONS

Search Report received in International Application No. PCT/EP2022/064893 dated Jul. 15, 2022, with translation, 6 pages.

*Primary Examiner* — Carolyn A Pehlke
(74) *Attorney, Agent, or Firm* — Christopher A. Rothe; CM Law

(57) ABSTRACT

A cannula attachment for a spinal cannula that can be used, for example, in spinal anesthesia. The cannula attachment has a body that extends between a proximal end and a distal end, a fluid channel that extends through the body, and an observation channel section visible from the outside through a transparent region of the body. At least one optical lens is arranged in the transparent region by which the observation channel section is visible with optical magnification. The observation channel section contains at least one optical prism configured for refraction and/or reflection of light incident into the observation channel section through the optical lens.

10 Claims, 5 Drawing Sheets

(56) References Cited

U.S. PATENT DOCUMENTS

| | | | |
|---|---|---|---|
| 8,551,059 | B2 | 10/2013 | Katerkamp et al. |
| 2002/0055715 | A1 | 5/2002 | Young et al. |
| 2011/0071480 | A1 | 3/2011 | Katerkamp et al. |

FOREIGN PATENT DOCUMENTS

| | | | |
|---|---|---|---|
| EP | 0522737 | A1 | 1/1993 |
| WO | 2009124751 | A1 | 10/2009 |
| WO | 2019070486 | A1 | 4/2019 |

* cited by examiner

NEEDLE ATTACHMENT FOR A SPINAL NEEDLE

CROSS-REFERENCE TO RELATED APPLICATIONS

This application is the United States national phase entry of International Application No. PCT/EP2022/064893, filed on Jun. 1, 2022, and claims priority to German Application No. 10 2021 205 601.6, filed on Jun. 2, 2021. The contents of International Application No. PCT/EP2022/064893 and German Application No. 10 2021 205 601.6 are incorporated by reference herein in their entireties.

FIELD

The invention relates to a cannula attachment for a spinal cannula, comprising a body which extends between a proximal end and a distal end, a fluid channel which extends through the body and which has an observation channel section visible from the outside through a transparent region of the body, and comprising at least one optical lens which is arranged in the transparent region and by means of which the observation channel section is visible with optical magnification.

BACKGROUND

Spinal cannulas are used, for example, as part of spinal anaesthesia for puncture of the spinal cord and comprise a cannula attachment and a hollow needle fixed thereto. During use, the hollow needle is advanced into the cerebrospinal fluid (CSF) space of the spinal cord that is filled with CSF. To confirm the correct position of the hollow needle, the fluid flashback entering the cannula attachment is visually monitored.

A cannula attachment configured for visual monitoring is disclosed by U.S. Pat. No. 6,656,161 B2, and it comprises a body, a hollow needle being fixable to the distal end thereof. A fluid channel extends between the distal end and a proximal end of the body. The fluid channel has an observation channel section which is referred to as a chamber. A wall of the body that is adjacent to the chamber is provided with an optical lens. This has the aim of making the chamber visually perceptible from the outside to an observer with magnification. The aim of this is to improve the detection of fluid flashback. Moreover, said patent document teaches that the chamber should have as small a volume as possible.

SUMMARY

It is an object of the present invention to provide a cannula attachment of the type mentioned at the beginning that allows improved visual monitoring of fluid flashback.

This object is achieved by there being present in the observation channel section at least one optical prism configured for refraction and/or reflection of light incident into the observation channel section through the optical lens. Owing to the light-refracting and/or light-reflecting optical properties of the at least one prism, an observer receives distinctly different visual perceptions and/or images, depending on whether the observation channel section is filled with air or with liquid. In principle, visual differences do occur even in the absence of the at least one prism. However, the visual differences are distinctly less obvious without a prism and are therefore more difficult for the observer to perceive. Owing to the at least one optical prism, it can therefore be established very clearly whether a fluid flashback is already taking place in the observation channel section or not. The inventors have recognized that the combination of, firstly, optical magnification and, secondly, light refraction and/or reflection allows particularly reliable and simple visual monitoring even under adverse lighting conditions. The cannula attachment can also be referred to as a cannula hub or as just a hub. The distal end of the body is configured for connection to a hollow needle of the spinal cannula. Preferably, the proximal end that is opposite in the longitudinal direction of the body is configured for connection to a further medical component, for example a syringe, a medical tubing line or the like. Fluid flashback occurs in the proximal direction. In one embodiment, the at least one optical prism is a component which is manufactured separately from the body and subsequently inserted into the observation channel section. In other embodiments, the at least one optical prism is integrally integrated into the body. The same applies, mutatis mutandis, with respect to the at least one optical lens. Accordingly, the at least one optical lens is manufactured as a separate component and subsequently attached to the body in one embodiment. In other embodiments, the at least one optical lens is integrally integrated into the body. The body is transparent at least in the region of the observation channel section, the at least one optical lens and/or the at least one optical prism. To this end, the body is made of a transparent material, preferably a plastic, at least sectionally.

In one embodiment, the at least one optical lens and the at least one optical prism are formed by the same transparent wall of the body and are thus integrally joined, the at least one optical lens being assigned to an outer face of the transparent wall and the at least one optical prism being assigned to an inner face of the transparent wall. This achieves a simplified structure of the cannula attachment, thereby simplifying production and assembly. The integrated construction of the at least one optical lens and the at least one optical prism in the body, more precisely the transparent wall thereof, can reduce the required number of components of the cannula attachment. The outer face of the transparent wall faces away from the observation channel section in the radial direction. The inner face of the transparent wall faces the observation channel section in the radial direction. The transparent wall of the body is arranged in the transparent region of the body or forms the transparent region of the body. The outer face of the transparent wall borders on an environment. The inner face of the transparent wall borders on the observation channel section.

In one embodiment, the fluid channel has a total volume, the observation channel section occupying a predominant volume fraction of the total volume. In other words, the observation channel section is as large as possible compared to the other dimensions of the fluid channel and/or the body. Accordingly, the observation channel section occupies the predominant volume fraction of the total volume of the fluid channel. The comparatively large dimensioning of the observation channel section means that a relatively low flow velocity of fluid flashback can be achieved. This is in relation to a comparatively small-dimensioned observation channel section. Owing to the slowed flow velocity, an observer has more time to visually perceive a fluid flashback that is occurring. The inventors have recognized that the reduced flow velocity is associated with further improved visual monitoring. As a result of the rapid visibility of fluid flashback, the observer can react more quickly, and so less fluid has to be aspirated. Moreover, CSF dripping out of the cannula attachment can be avoided. Consequently, fluid flashback only being detected when fluid is dripping out, and the patient losing fluid as a result, can also be avoided. As a result, adverse effects on the health of the patient can be avoided. In particular, the risk of so-called postdural puncture headache (PDPH) is reduced.

In one embodiment, the fluid channel has a maximum internal diameter which is not more than 45%, preferably not more than 10%, greater than a maximum internal diameter of the observation channel section. In other words, the observation channel section has a largest possible internal diameter in relation to the other diameter dimensions of the fluid channel in this embodiment. Preferably, the internal diameter of the fluid channel is variable over the longitudinal extent thereof. Accordingly, the fluid channel has channel sections which are relatively narrow and relatively wide in diameter. The diameter of the observation channel section is as wide as possible. In one embodiment, the maximum internal diameter of the observation channel section is the maximum internal diameter of the entire fluid channel. Owing to the relatively large maximum internal diameter of the observation channel section, a relatively low flow velocity of fluid flashback is achieved. For the associated advantages, reference is made to the explanations in connection with the preceding embodiment. What has been stated there also applies, mutatis mutandis, to this embodiment of the invention. The internal diameter can also be referred to as a hydraulically effective diameter or hydraulic diameter and can, in this respect, have the dimension of an area.

In one embodiment, the proximal end of the body has a standardized fluid connector having a standardized internal diameter, the maximum internal diameter of the observation channel section being not more than 45%, preferably not more than 10%, smaller than the standardized internal diameter of the fluid connector. This embodiment also has a comparatively large internal diameter of the observation channel section, the internal diameter being defined in relation to the standardized internal diameter of the standardized fluid connector. This embodiment also allows a lowest possible flow velocity of fluid flashback within the observation channel section. For the associated advantages, reference is made to what has been stated above. In one embodiment, the standardized fluid connector is an NRFit connector in accordance with DIN EN ISO 80369-6, the maximum internal diameter of the observation channel section being not more than 20%, preferably not more than 15%, particularly preferably not more than 10%, smaller than the standardized internal diameter of the NRFit connector. In another embodiment, the fluid connector is a Luer connector in accordance with DIN EN ISO 80369-7, the maximum internal diameter of the observation channel section being not more than 45%, preferably not more than 30%, smaller than the standardized internal diameter of the lure connector.

In one embodiment, at least two optical prisms and at least two optical lenses, pairs of which in the form of lens-prism pairs are arranged angularly offset to each other in the circumferential direction of the observation channel section, are present. As a result of the angularly offset arrangement of multiple lens-prism pairs, visual monitoring can be carried out by an observer at different viewing angles relative to the body. In other words, the observer can monitor fluid flashback not only in a single viewing direction toward the body, but also in different viewing directions. This further improves visual monitoring. If there are exactly two lens-prism pairs, they are preferably arranged angularly offset to each other by 90° or 180°. In the case of an angular offset of 90°, monitoring can be carried out, for example, viewing in the direction of an upper face and a right and/or left side of the body. In the case of an angular offset of 180°, monitoring can be carried out through opposite faces of the body. If there are more than two lens-prism pairs, the angular offset thereof is preferably the quotient from a 360° circumferential angle of the observation channel section and the number of lens-prism pairs. For example, if there are ten lens-prism pairs, the angular offset thereof is preferably 36°.

In one embodiment, a first lens-prism pair is arranged on a first face, preferably an upper face, of the body and a second lens-prism pair is arranged on a second face, preferably an opposite lower face, of the body. Firstly, this embodiment of the invention allows visual monitoring at different viewing angles. At the same time, a comparatively large and effective internal diameter of the observation channel section can be maintained. The inventors have recognized that, on the one hand, the arrangement of as many angularly offset prisms as possible in the observation channel section does have a positive effect on visual monitoring. On the other hand, this reduces the effective diameter of the observation channel section. This can lead to a relatively high flow velocity of fluid flashback, which in turn can have an adverse effect on visual monitoring. The embodiment with two lens-prism pairs forms a kind of optimum in this respect.

In one embodiment, the body in the region of the observation channel section has a cuboid shape with pairs of opposite outer faces, the at least one optical lens being assigned to one of the outer faces. The cuboid shape of the body in the region of the observation channel section allows the latter to be dimensioned comparatively large. Moreover, the cuboid shape supports the handling of the cannula attachment, since the pairs of opposite outer faces can be gripped between the fingers of a hand ergonomically in an advantageous manner. Moreover, the cuboid shape allows simple visual monitoring of the angular orientation of the cannula attachment. To further simplify this monitoring, the body can have a marking section on one of its outer faces, preferably its upper face. This can be, for example, in the form of a recess, a projection or the like.

In one embodiment, the body is made of a transparent plastic material in one piece. Firstly, this simplifies production since different materials for different sections of the body can be dispensed with. Secondly, the completely transparent design of the body supports the incidence of light into the observation channel section. This can achieve further improved visual monitoring of fluid flashback.

The present invention further relates to a spinal cannula comprising a cannula attachment as described above and comprising a hollow needle fixed to the cannula attachment. The hollow needle is fixed to the distal end of the cannula attachment. The hollow needle is elongate between a sharpened distal end and a proximal end in a manner known to a person skilled in the art and has a continuous lumen. The lumen of the hollow needle is fluidically connected to the fluid channel of the cannula attachment in a manner known in principle.

BRIEF DESCRIPTION OF THE DRAWINGS

Further advantages and features of the invention will become apparent from the following description of a preferred embodiment of the invention that is illustrated by means of the drawings.

DETAILED DESCRIPTION

Figure 1:
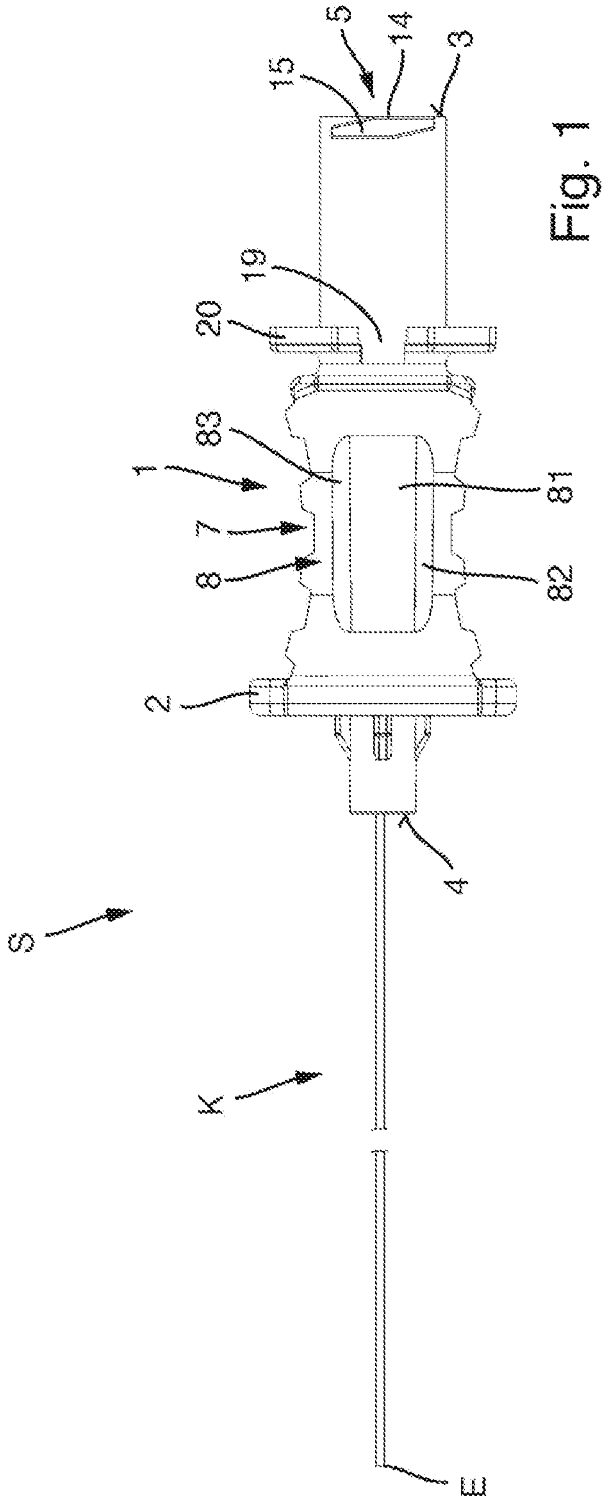
FIG. 1 shows a schematic top view of one embodiment of a spinal cannula according to the invention comprising one embodiment of a cannula attachment according to the invention and comprising a hollow needle fixed to the cannula attachment.

According to FIG. 1, a spinal cannula S is intended for use in spinal anaesthesia and comprises a hollow needle K and a cannula attachment 1.

The hollow needle K is designed in a manner known to a person skilled in the art and is intended for puncture of the spinal cord. In this respect, the hollow needle K is elongate between a proximal end which is not further identified and a distal end E, the latter being provided with a sharpened cannula tip. The proximal end of the hollow needle K is fixed in a receiving recess A (FIGS. 6 and 8) of the cannula attachment 1 in a manner known to a person skilled in the art. For example, the proximal end of the hollow needle K can be bonded into the receiving recess A.

Figure 2:
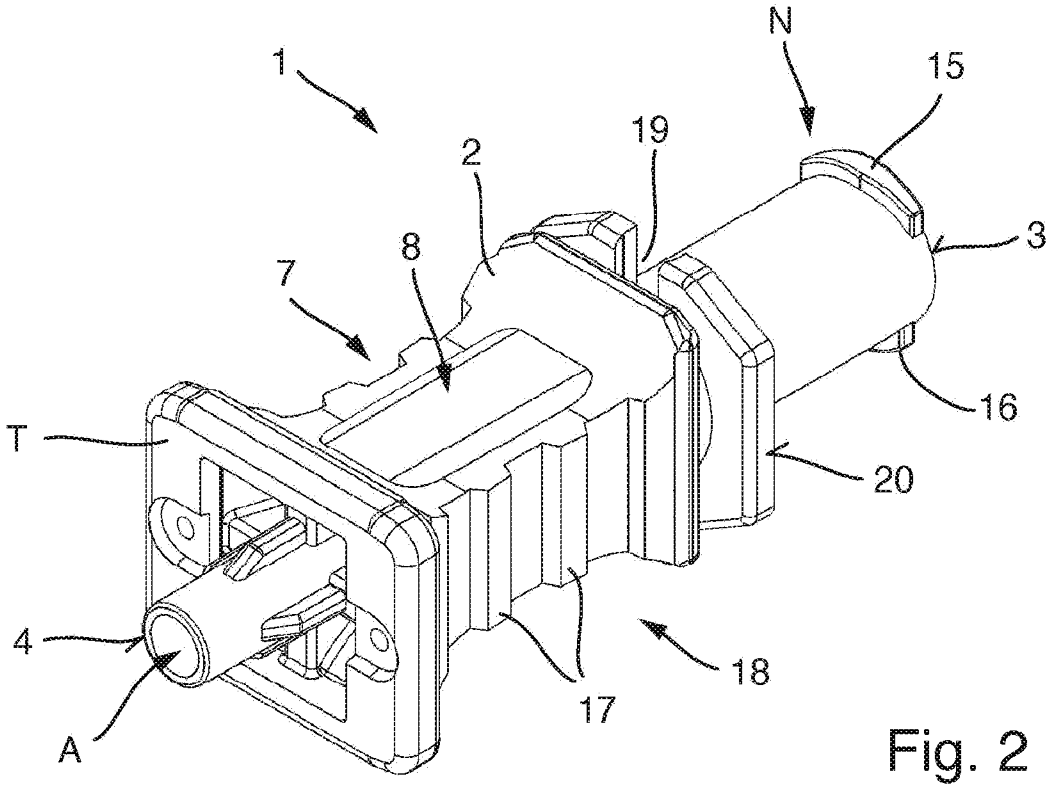
FIG. 2 shows a schematic perspective view of the cannula attachment as viewed facing a distal end.

The cannula attachment 1 can also be referred to as a cannula hub or hub and comprises a body 2 which extends between a proximal end 3 and a distal end 4. Furthermore, the cannula attachment 1 comprises a fluid channel 5 which extends through the body 2 and which has an observation channel section 6. The observation channel section 6 is visible from the outside through a transparent region 7 (FIG. 2) of the body 2. Furthermore, the cannula attachment 1 comprises at least one optical lens 8 arranged in the transparent region 7. By means of the optical lens 8, the observation channel section 6 is visible from the outside with optical magnification.

When using the spinal cannula S, the spinal cord is punctured by means of the hollow needle K. To monitor the correct position of the distal end E in the region of the spinal cord, cerebrospinal fluid (CSF) is aspirated through the hollow needle K into the cannula attachment 1. Once there is a corresponding fluid flashback in the proximal direction, a correct position of the distal end E can be assumed. The observation channel section 6 arranged in the transparent region 7 allows visual monitoring of said fluid flashback. The at least one optical lens 8 supports the visual monitoring by means of optical magnification of the observation channel section 6.

Figure 4:
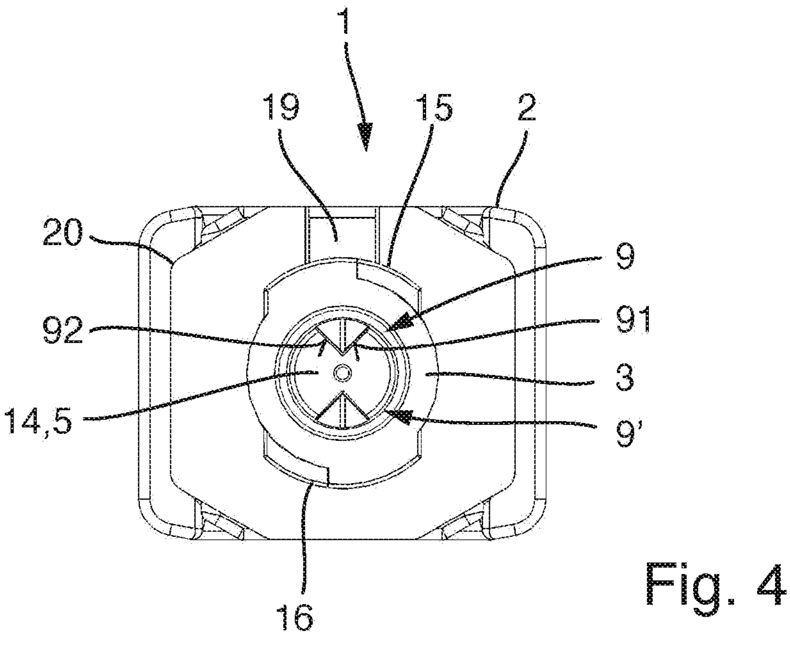
FIG. 4 shows a schematic rear view of the cannula attachment as viewed in the distal direction.
Figure 6:
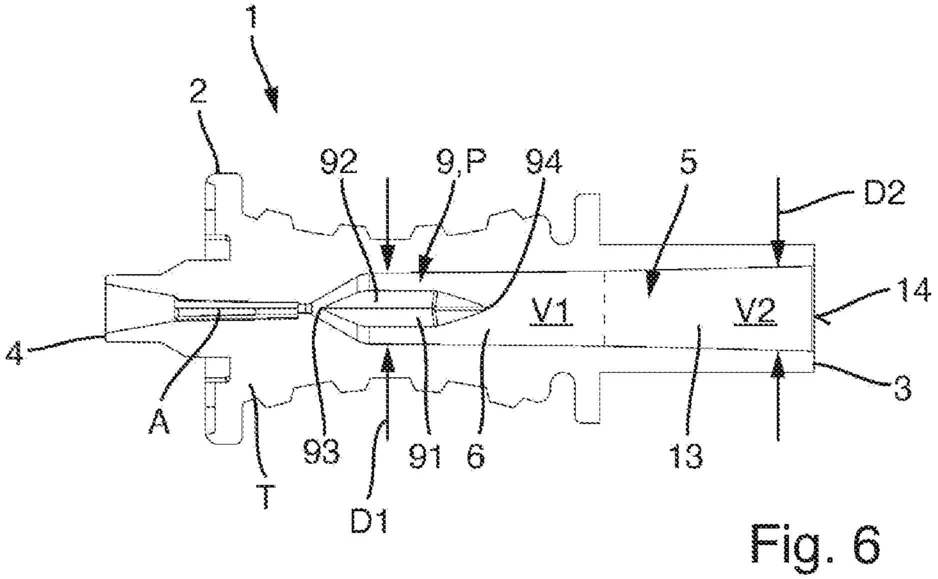
FIG. 6 shows a schematic longitudinal section of the cannula attachment along a section VI-VI as per FIG. 5.
Figure 8:
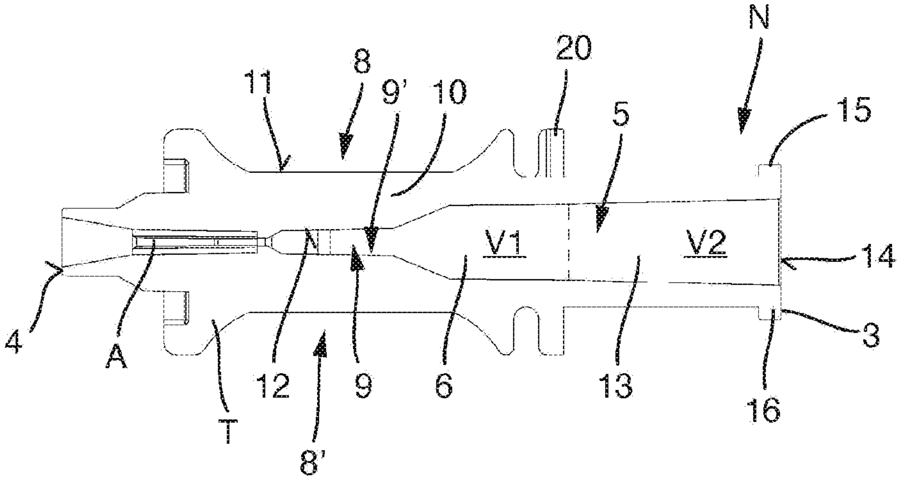

In order to allow further improved visual monitoring, the cannula attachment 1 also comprises at least one optical prism 9, which is shown by means of FIGS. 4, 6 and 8. The optical prism 9 is arranged in the observation channel section 6 and is configured for refraction and/or reflection of light incident into the observation channel section 6 through the transparent region 7 and/or the optical lens 8. Because of its light-refracting and/or light-reflecting properties, the prism 9 allows distinctly improved visual monitoring of fluid flashback. This is because the observer receives distinctly different visual perceptions, depending on whether the observation channel section 6 is filled with air or liquid. Fluid flashback is, of course, perceptible in principle even without the prism 9. However, this is to a distinctly reduced extent. The present combination of optical prism 9 and optical lens 8 allows reliable monitoring of fluid flashback even under adverse visual conditions, for example under poor lighting conditions.

Further structural and functional features of the cannula attachment 1 will be explained below. The features explained below, notwithstanding their possible advantages, are not necessarily to be considered essential with respect to the present invention.

In the embodiment shown, the optical lens 8 and the optical prism 9 are formed by the same transparent wall 10 of the body 2. This is shown in detail by means of FIG. 8. The optical lens 8 and the optical prism 9 are thereby integrally joined. The optical lens 8 is assigned to an outer face 11 of the transparent wall 10. The optical prism 9 is assigned to an inner face 12 of the transparent wall 10. The outer face 11 faces an environment which is not further identified. The inner face 12 faces the observation channel section 6.

In the present case, the body 2 is made of a transparent plastic material T in one piece. In this respect, the body 2 is see-through not only in the transparent region 7, but also away from it. In embodiments not depicted in a drawing, a multipart design can also be provided instead of a one-piece design of the body. In addition, in further embodiments, the body is see-through only in its transparent region.

Figure 7:
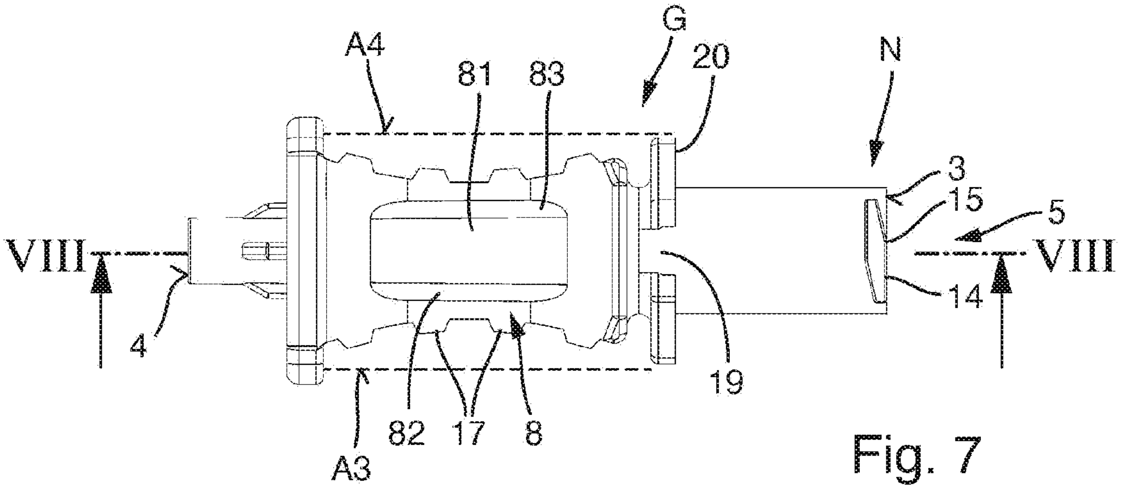
FIG. 7 shows a schematic plan view of the cannula attachment and FIG. 8 shows a further longitudinal section of the cannula attachment along a section VIII-VIII.

The fluid channel 5 is elongate between the proximal end 3 and the distal end 4. Starting from the proximal end 3, the fluid channel 5 initially has a proximal channel section 13, which opens into a proximal channel opening 14 in the proximal direction. In the distal direction, the proximal channel section 13 opens into the observation channel section 6. The observation channel section 6 opens into the receiving recess A in the distal direction. In the region of the dashed line drawn in for illustration in FIGS. 6 and 8, the fluid channel 5 is subdivided into, firstly, the proximal channel section 13 and, secondly, the observation channel section 6. This subdivision is to be understood as illustrative. In any case, the observation channel section 6 is formed by the section of the fluid channel 5 that extends directly below the optical lens 8 in the plan view (FIGS. 1 and 7).

The fluid channel 5 has a total volume V1, V2. In the embodiment shown, the total volume V1, V2 is composed of a first volume fraction V1 of the observation channel section 6 and a second volume fraction V2 of the proximal channel section 13. In other words, the total volume V1, V2 is the sum of the first volume fraction V1 and the second volume fraction V2 in the present case. In the embodiment shown, the first volume fraction V1 of the observation channel section 6 is dimensioned as large as possible. This is in relation to the second volume fraction V2. In preferred embodiments, the first volume fraction V1 occupies a large portion of the total volume V1, V2. As a result of the first volume fraction V1 being dimensioned as large as possible, a relatively low flow velocity of fluid flashback when entering the observation channel section 6 is achieved. This has been found to be particularly advantageous for various reasons.

Furthermore, with reference to FIG. 6, the fluid channel 5 has a maximum internal diameter D2 in the embodiment shown. In the present case, it is situated in the region of the proximal channel section 13, more precisely in the region of the channel opening 14. The observation channel section 6 has a maximum internal diameter D1. In the embodiment shown, the maximum internal diameter D1 of the observation channel section 6 corresponds approximately to the maximum internal diameter D2 in the region of the proximal channel section 13. Accordingly, the internal diameter, or hydraulic diameter, of the observation channel section 6 is dimensioned as large as possible in relation to the internal diameter, or hydraulic diameter, of the fluid channel 5. This supports a reduction of the flow velocity of fluid flashback in the region of the observation channel section 6. In the embodiment shown, the maximum internal diameter D1 of the observation channel section 6 is present in the longitudinal section plane which can be seen from FIG. 6. In a longitudinal section plane rotated by 90° according to FIG. 8, a different internal diameter arises. This is because of the at least one prism 9. With respect to said reduction in flow velocity, a narrowing in one plane is not significant. Instead, it is more critical that the observation channel section 6 has a comparatively largest possible effective hydraulic diameter.

In preferred embodiments, the maximum hydraulic diameter of the observation channel section is not more than 45%, particularly preferably not more than 10%, smaller than a maximum hydraulic diameter of the proximal channel section 13.

In the region of a proximal end 3, the body 2 is configured for detachable connection to a fluid-guiding medical component, such as a syringe, a medical tubing line or the like. For this purpose, the body 2 has a standardized fluid connector N at its proximal end 3. In the present case, the fluid connector N is an NRFit connector known to a person skilled in the art. It has connecting elements 15, 16 which are arranged angularly offset to each other in the circumferential direction of the proximal end 3. The connecting elements 15, 16 are configured for detachable interlocking connection to complementary connecting elements of a correspondingly complementary NRFit connector. The fluid connector N complies with a DIN EN ISO 80369-6 standard. The standardization comprises not only the shaping of the connecting elements 15, 16, but also the design of the proximal channel section 13, more precisely the internal diameter D2 and/or inner contour thereof. Furthermore, with reference to FIG. 6, the observation channel section 6 merges into the proximal channel section 13 dimensionally standardized in this respect in the proximal direction without a reduction in cross-section or practically without a significant reduction in cross-section. Owing to the manufacturing process, a draft of approximately 1° to 3° may be present.

In one embodiment not depicted in a drawing, the fluid connector is a Luer connector, more precisely a Luer lock connector, in accordance with DIN EN ISO 80369-7. In the embodiment with a Luer connector, a slightly larger reduction in cross-section may be present.

Figure 3:
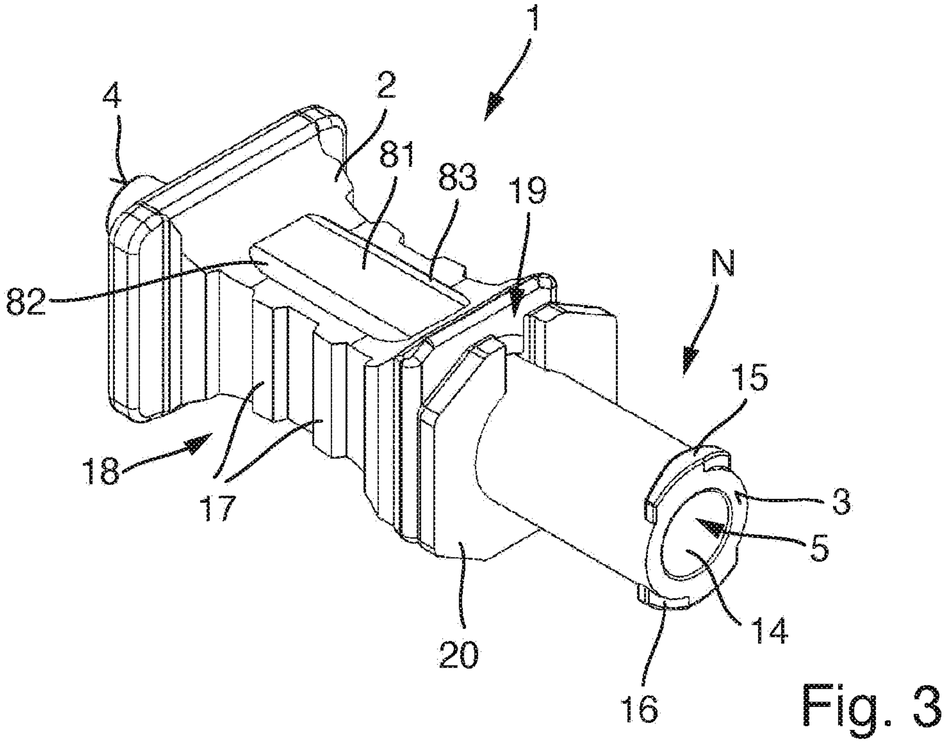
FIG. 3 shows a further schematic perspective view of the cannula attachment as viewed facing a proximal end.

The optical lens 8 has different lens sections 81, 82, 83 in the region of the outer face 11 of the transparent wall 10 (FIGS. 1, 3 and 7). They can also be referred to as central section 18, medial section 82, and lateral section 83. The central section 81 has a planar outer contour, and so there is no curvature, especially in the longitudinal direction of the observation channel section 6. In the transverse direction as well, the central section 81 has no curvature in the present case. In contrast, the medial section 82 and the lateral section 83 are in any case inclined and/or curved in the transverse direction. The inclination and/or curvature is inwardly directed in the radial direction of the observation channel section 6 proceeding from the central section 81.

In the embodiment shown, the optical lens 8 is at least substantially, preferably completely, elongate over an entire length of the observation channel section 6. In further embodiments, the optical lens 8 has a different design.

The optical prism 9 is in the form of a roof prism P in the embodiment shown. The optical prism 9 has a triangular cross-sectional area and/or prism faces 91, 92 which inwardly run toward each other in the radial direction of the observation channel section 6 and which can also be referred to as first prism face 91 and second prism face 92. The prism faces 91, 92 form boundary faces of the observation channel section 6. The prism 9 has end faces 93, 94 which are arranged opposite each other in the longitudinal direction of the observation channel section 6. In the region of the end faces 93, 94, the prism 9 is flattened at an acute angle. In embodiments not depicted in a drawing, the at least one prism has a different design. For example, the prism can be in the form of a triple prism.

In the embodiment shown, the longitudinal extent of the prism 9 corresponds to the longitudinal extent of the lens 8. The prism 9 is arranged below the central section 81 of the lens 8 in the radial direction of the observation channel 6. In the transverse direction of the central section 81, the prism 9 is centrally oriented. A common edge of the prism faces 91, 92 lies centrally below the central section 81.

Figure 5:
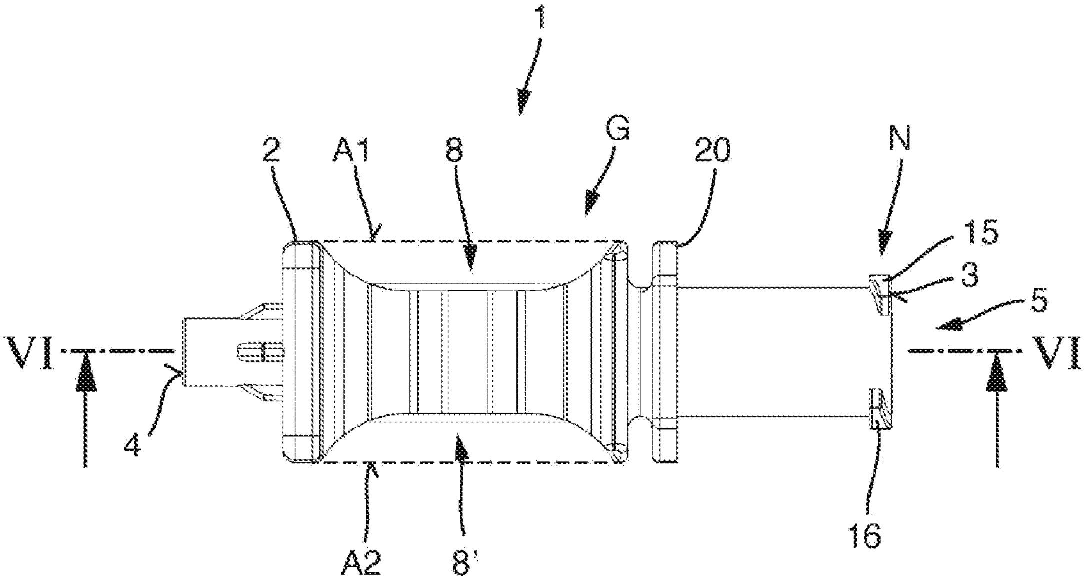
FIG. 5 shows a schematic side view of the cannula attachment.

In the embodiment shown, the cannula attachment 1 has two optical prisms 9, 9' (FIG. 4) and two optical lenses 8, 8' (FIG. 5). They can also be referred to as first lens 8 and second lens 8' and as first prism 9 and second prism 9'. In the embodiment shown, the prisms 9, 9' and the lenses 8, 8' form a first lens-prism pair 8, 9 and a second lens-prism pair 8', 9'.

With respect to the design and functioning of the second lens 8' and the second prism 9', what has already been stated in relation to the first lens 8 and the first prism 9 applies mutatis mutandis. In this respect, further explanations in this connection are unnecessary.

The first lens-prism pair 8, 9 and the second lens-prism pair 8', 9' are arranged angularly offset to each other in the circumferential direction of the observation channel section 6. The angular offset is 180° in the embodiment shown, and so said pairs are diametrically opposed in relation to the observation channel section 6.

In one embodiment not depicted in a drawing, only a single lens-prism pair is present. In further embodiments, more than two lens-prism pairs are present, in particular three, four, five, six or more. Moreover, in a further embodiment, the angular offset is 90°, instead of the 180° shown here.

In the present case, the body 2 in the region of the observation channel section 6 has a cuboid shape with pairs of opposite outer faces A1, A2 (FIG. 5) and A3, A4 (FIG. 7). It will be understood that there is no exact cuboid shape, but merely a basically cuboid shape. The outer faces A1 to A4 can also be referred to as upper face A1, lower face A2, medial face A3 and lateral face A4. The first lens-prism pair 8, 9 is assigned to the upper face A1. The second lens-prism pair 8', 9' is assigned to the lower face A2. In the present case, the medial face A3 and the lateral face A4 are each provided with a ribbing 18 having multiple projections 17. The ribbings 18 facilitate gripping and manipulation of the cannula attachment 1 between the fingers of a hand.

In the embodiment shown, the body 2 has a plate 20. The plate 20 is arranged in the region of said subdivision between the observation channel section 6 and the proximal channel section 13 in the longitudinal direction of the fluid channel 5. The plate 20 outwardly projects from the fluid connector N in the radial direction. The plate 20 can serve, for example, as an axial stop for a complementary fluid connector and can accordingly also be referred to as a stop plate. Whether a stop is present also depends, of course, on the particular design of the complementary fluid connector.

Furthermore, the body 2 has a marking section 19 which marks an alignment oriented around the longitudinal axis of the body 2. In the present case, the marking section 19 is assigned to the upper face A1. Moreover, the marking section 19 is in the form of a radially inwardly recessed notch on the plate 20 that is not further identified.

The invention claimed is:

1. A cannula attachment for a spinal cannula, the cannula attachment comprising:

a body which extends between a proximal end and a distal end;

a fluid channel which extends through the body and which has an observation channel section visible from outside the body through a transparent region of the body;

at least one optical lens which is arranged in the transparent region and by which the observation channel section is visible with optical magnification; and at least one optical prism is present in the observation channel section and configured for refraction and/or reflection of light incident into the observation channel section through the at least one optical lens.

2. The cannula attachment according to claim 1, wherein the at least one optical lens and the at least one optical prism are formed by a transparent wall of the body and are integrally joined, the at least one optical lens being assigned to an outer face of the transparent wall and the at least one optical prism being assigned to an inner face of the transparent wall.

3. The cannula attachment according to claim 1, wherein the fluid channel has a total volume, and wherein the observation channel section occupies a predominant volume fraction of the total volume.

4. The cannula attachment according to claim 1, wherein the fluid channel has a maximum internal diameter which is not more than 45% greater than a maximum internal diameter of the observation channel section.

5. The cannula attachment according to claim 1, wherein the proximal end of the body has a standardized fluid connector having a standardized internal diameter, and wherein a maximum internal diameter of the observation channel section is not more than 45% smaller than the standardized internal diameter of the fluid connector.

6. The cannula attachment according to claim 1, wherein the at least one optical lens comprises at least two optical lenses and the at least one optical prism comprises at least two optical prisms, the at least two optical lenses and the at least two optical prisms forming lens-prism pairs that are arranged angularly offset to each other in a circumferential direction of the observation channel section.

7. The cannula attachment according to claim 6, wherein a first lens-prism pair of the lens-prism pairs is arranged on a first face of the body, and a second lens-prism pair of the lens-prism pairs is arranged on a second face of the body.

8. The cannula attachment according to claim 1, wherein the body has a cuboid shape in a region of the observation channel section with a plurality of opposite outer faces, the at least one optical lens being assigned to one of the plurality of opposite outer faces.

9. The cannula attachment according to claim 1, wherein the body is made of a transparent plastic material in one piece.

10. A spinal cannula comprising:

a cannula attachment according to claim 1; and a hollow needle fixed to the cannula attachment.

* * * * *